United States Patent [19]
Pickart

[11] Patent Number: 5,858,993
[45] Date of Patent: Jan. 12, 1999

[54] STARCH-METAL COMPLEXES FOR SKIN AND HAIR

[75] Inventor: Loren R. Pickart, Bellevue, Wash.

[73] Assignee: Skin Biology, Inc., Bellevue, Wash.

[21] Appl. No.: 713,586

[22] Filed: Sep. 13, 1996

Related U.S. Application Data

[63] Continuation of Ser. No. 219,681, Mar. 28, 1994, abandoned.

[51] Int. Cl.$^6$ .......................... A61K 31/715; A61K 33/24; A61K 33/34

[52] U.S. Cl. .......................... 514/60; 424/445; 424/446; 424/447; 514/493; 514/499; 514/500; 514/887; 514/928

[58] Field of Search ............................. 514/60, 493, 499, 514/500, 887, 928; 424/445, 446, 447

[56] References Cited

U.S. PATENT DOCUMENTS

| | | |
|---|---|---|
| 3,758,682 | 9/1973 | Huber et al. . |
| 3,812,252 | 5/1974 | Silvetti . |
| 4,053,630 | 10/1977 | Yu et al. . |
| 4,123,511 | 10/1978 | Heintze . |
| 4,156,737 | 5/1979 | Bertelli . |
| 4,203,435 | 5/1980 | Krull et al. . |
| 4,283,386 | 8/1981 | Van Scott et al. . |
| 4,414,202 | 11/1983 | Silvetti . |
| 4,440,754 | 4/1984 | Sorenson . |
| 4,461,725 | 7/1984 | Konishi . |
| 4,503,047 | 3/1985 | Banfi et al. . |
| 4,551,431 | 11/1985 | Pierce . |
| 4,728,642 | 3/1988 | Pawelchak et al. . |
| 4,760,051 | 7/1988 | Pickart . |
| 4,767,753 | 8/1988 | Pickart . |
| 4,797,392 | 1/1989 | Chernomorsky ............ 514/185 |
| 4,863,897 | 9/1989 | Pickart . |
| 4,889,844 | 12/1989 | Silvetti . |
| 5,000,950 | 3/1991 | Wuendisch . |
| 5,118,665 | 6/1992 | Pickart . |
| 5,164,367 | 11/1992 | Pickart . |
| 5,177,065 | 1/1993 | Silvetti, Sr. . |
| 5,401,758 | 3/1995 | Atwal et al. ............ 514/353 |

FOREIGN PATENT DOCUMENTS

| | | |
|---|---|---|
| 66283 | 12/1982 | European Pat. Off. . |
| 189182 | 7/1986 | European Pat. Off. . |
| 190736 | 8/1986 | European Pat. Off. . |
| 288278 | 10/1988 | European Pat. Off. . |
| 450398 | 10/1991 | European Pat. Off. . |
| 2139512 | 2/1972 | Germany . |
| 3226753 | 1/1984 | Germany . |
| 2044265 | 10/1980 | United Kingdom . |
| 2097256 | 11/1982 | United Kingdom . |
| 88/08695 | 11/1988 | WIPO . |
| 88/08851 | 11/1988 | WIPO . |
| 89/12441 | 12/1989 | WIPO . |
| 91/03488 | 3/1991 | WIPO . |
| 91/05797 | 5/1991 | WIPO . |
| 91/07431 | 5/1991 | WIPO . |
| 91/12267 | 8/1991 | WIPO . |
| 91/14437 | 10/1991 | WIPO . |
| 94/07448 | 4/1994 | WIPO . |

OTHER PUBLICATIONS

Carraher et al., "Biological Activities of Hydroxyl–Containing Natural Products Emphasizing Tin–Containing Products," *Biotechnol. Polymer.*, 34–40 (1993).

Johnson et al., "Cytotoxic Chelators and Chelates Inhibition of DNA Synthesis in Cultured Rodent and Human Cells by Aroylhydrazones and by a Copper (II) Complex of Salicylaldehyde Benzoyl Hydrazone", *Inorg. Chem. Acta* 67:159–165 (1982).

Raju et al., "Ceruloplasmin, Copper Ions, and Angiogenesis", *J. Natl. Cancer Inst.* 69:1183–1188 (Nov., 1982).

Pickart et al., "Inhibition of the Growth of Cultured Cells and an Implanted Fibrosarcoma by Aroylhydrazone Analogs of the Gly–His–Lys–Cu(II) Complex", *Biochem. Pharm.* 32:3868–3871 (1983).

Pickart et al., "The Biological Effects and Mechanism of Action of the Plasma Tripeptide Glycyl–L–histidyl–L–lysine", *Lymphokines* 8:425–446 (1983).

Sorenson, "Copper Complexes: A Physiologic Approach to Treatment of Chronic Diseases", *Comprehensive Therapy* 11 (4) :49–64 (1985).

Bergren et al. "Improved Survival Using Oxygen Free Radical Scavengers in the Presence of Ischemic Bowel Anastomosis", (*Am. Surg.* 54:333–336 (Jun., 1988)).

Holloway, et al., "Multicenter Trial of Cadexomer Iodine to Treat Venous Stasis Ulcer," *West J. Med.*, 151:35–38 (1989).

Niwa, "Lipid Peroxides and Superoxide Dismutase (SOD) Induction in Skin Inflammatory Diseases, and Treatment with SOD Preparations", *Dermatologica* 179 S1: 101–106 (1989).

Chandy, et al., *Biomater. Artif. Cells Artif Organs,* 18:1–24 (1990).

Primary Examiner—Richard L. Raymond
Attorney, Agent, or Firm—Townsend and Townsend and Crew

[57] ABSTRACT

Methods are provided for preparing compositions suitable for protecting irritated or damaged skin from further oxidative and biochemical damage and thus permitting natural healing processes to progress, for accelerating the rate of healing of burns and surgical wounds, and for increasing the size of hair follicles and the rate of hair growth. The compositions generally comprise precipitates formed by the complexation of starch of various plants with ionic transition metals, such as copper(II) and tin(II) salts.

18 Claims, No Drawings

STARCH-METAL COMPLEXES FOR SKIN AND HAIR

This is a Continuation of application Ser. No. 08/219,681, filed Mar. 28, 1994, now abandoned.

BACKGROUND OF THE INVENTION

Restoring the function of damaged and wounded skin continues to be a major health problem despite the development of various medications. Many approaches to skin-healing that are currently being developed, such as the production of growth factor proteins and pharmaceutical drugs with wound healing properties, and occlusive dressings for wounds, are beyond the economic reach of many patients. A major need exists for improved and low cost skin-care products and medicaments in less-developed countries, particularly in the tropics, where conditions such as inadequate health care, widespread skin fungal diseases, and the use of flammables such as kerosene for cooking and similar conditions give rise to high incidents of serious skin injury. For such countries, there is a critical need is to produce effective medicines that can be produced at very low cost using readily available materials. Even in more developed countries the increasing demands for cost-containment in medical services necessitate the development of low-cost products for skin care and pharmaceuticals for wound healing. Procedures such as hospitalization for the treatment of diabetic skin ulcers are increasingly being restricted. Thus, improved and cost-effective treatments for wound healing are required for the future.

Delayed healing or incomplete healing in humans and other animals causes additional pain and suffering for the patient and markedly increases wound complications and medical costs. Often the wound continues as a chronic sore that requires extensive attention and medical care to control infection and tissue necrosis. Even when such wounds finally heal, the wound area is frequently devoid of the ability to respond to tactile stimulation and is often filled with excessive deposits of immature collagen that produces permanent scarring. The urgent need for improved wound-healing compositions extends to wounds generated by surgical procedures. The success of surgical procedures, especially in very ill or elderly patients, is typically a function of the adequacy and speed of post-surgical healing.

Another aspect that can impair the normal healing response is excessive inflammation of injured or wounded skin. While the inflammatory process and its concomitant influx of white cells into the afflicted area are an integral part of the natural healing process, in some cases the inflammatory process becomes excessive and delays healing. The wounded tissue becomes locked in an early phase of the healing process and cannot proceed to completion. In such instances, compounds with anti-inflammatory activities are used to allow the process to proceed normally. One promising approach for the therapeutic treatment of conditions associated with inflammation and impaired wound healing has been the use of metal ions complexed to organic molecules or amino acids, amino acid derivatives and peptides. Some of these complexes possess anti-inflammatory activity, while others possess both anti-inflammatory activity and healing actions. Yet other complexes reportedly possess hair-growth stimulating actions in addition to anti-inflammatory and/or healing activities, as described in, for example, applicant's co-owned pending patent application Ser. No. 07/954,620, now U.S. Pat. No. 5,382,431, which is incorporated in its entirety by reference herein.

The use of copper salts or complexes as anti-inflammatory agents for the healing of stomach ulcers in the treatment of patients suffering from acute or chronic arthritis dates back to the 1940's and 1950's (see, e.g., reviews by Sorenson, *Inflammation*, 3:317–331 (1976); *Agents and Actions* 8:305–331 (1981), and *Comprehensive Therapy* 11:49–64 (1985)). The use of copper salts and complexes, such as copper-salicylate complex, seems to have been abandoned, apparently due to the early promise of the steroidal anti-inflammatories, such as hydrocortisone. Other complexes of copper with amino acids (tryptophan, lysine), with non-steroidal anti-inflammatory drugs (indomethacin, ketoprofen, acetylsalicylic acid) or with fatty acids (oleic, lauric and caprylic acids) have been studied but, despite their promise, were rarely developed beyond the preclinical phases, apparently due to problems of irritation, toxicity, and inadequate efficacy.

While many copper-complexes have been reported to possess anti-inflammatory properties, a more limited group have been reported to also possess healing actions. Heintze (U.S. Pat. No. 4,123,511) reported that a copper oleate complex had anti-inflammatory and skin healing activity. Sorenson (U.S. Pat. No. 4,440,754) describes the use of complexes of copper(II) salts and amino acids, such as tryptophan or lysine, or with organic molecules such as 3,5-diisopropylsalicylic acid, acetylsalicylic acid or salicylic acid, to prevent and heal gastrointestinal ulcers. Using a wound-healing model, Townsend and Sorenson (Sorenson et al., *Agents and Actions* 8:305–325 (1981)) found salicylate-copper to accelerate the rate of healing and to improve the quality of healing of surgically-induced ulcers in rats. Also, Sorenson wrote (ibid. and *Inflammation* 3: 317–331 (1976)) that Townsend demonstrated that copper(II)-(tryptophan)2 increased the rate of ulcer healing in a surgically-induced ulcer model. The increased healing was purportedly due to a more rapid re-epithelialization of the wound and an increase in the quantity and quality of the collagen. Fine collagen fibers in a normal orientation developed in treated animals, in contrast to non-treated animals in which the new collagen was very dense and composed of thick, wavy disoriented bundles, resembling scar tissue.

Federici and Bertolotto (EP 450,398 and IT 9,019,948) reports that chondroitin sulfate-copper(II) complexes possessed anti-inflammatory activity. European Patent No. EP 66,283 discloses "eustatic" compositions which contain a non-toxic metal ion (including copper) and a glycosaminoglycan of hyaluronic acid or chondroitin sulfate useful as a cicatrizant (wound healing by closure).

UK Patent Application GB 2 044 265 describes metal complexes (including copper) of adenosine triphosphate as aiding the recovery of bone tissue in cases of fractures as well as in osteoporosis and bone cysts.

Konishi (U.S. Pat. No. 4,461,724) reports that the tetrapeptide Gly-Ser-His-Lys and peptides of related structures possess anti-inflammatory and healing actions when complexed with metals such as ionic copper and zinc.

Yu (U.S. Pat. No. 4,053,630) discloses the use of cysteic acid and its derivatives cysteine sulfinic acid or homocysteic acid, chelated to metal ions such as ferric, cupric, zinc or aluminum, to form compositions that alleviate symptoms of diseases characterized by defects of keratinization and achieved a remission of ichthyosis, dandruff and acne. Bertelli (U.S. Pat. No. 4,156,737) suggests that copper complexes of p-aminomethyl-benzene-sulfonamide possess healing and protective effects on skin burns. Van Scott (U.S. Pat. No. 4,283,386) reports that metallic (copper, zinc, or aluminum) salt forms of cysteic acid, cysteine sulfinic acid and homocysteic acid have therapeutic actions that produce remissions of dry and broken skin, keratoses, warts and palmar and plantar hyperkeratosis.

Niwa (*Dermatologica* 179 S1: 101–106 (1989)) and Bergren et al. (*Am. Surg.*, 54: 333–336 (1988)) found that the anti-inflammatory protein Cu, Zn-superoxide dismutase also acts to enhance healing processes.

Pickart (see, e.g., PCT Publications WO 91/14437, WO 91/12267, WO 91/05797, WO 91/03488, WO 89/12441, WO 88/26448, WO 88/08851, EP Patents EP 190,736, EP 189,182; and U.S. Pat. No. 4,767,753) describes the synthesis and use of metal complexes of Gly-L-His-L-Lys as anti-inflammatory and healing agents.

A number of metal complexes have been used to promote hair growth. Yamashiki (Japan Pat. 70018997) used a complex of copper-pantothenate to purportedly promote growth of hair roots and promote skin functions. Morelle (U.K. Pat. GB 2097256, DE Pat. 32212448) used amino acid derivatives (N-butyryl amino acids) complexed with copper and other metals for cosmetic and therapeutic purposes, including use as hair and skin stimulants. Banfi et al. (U.S. Pat. No. 4,503,047) disclose a composition containing primarily one or more sulfur-containing amino acid(s) and copper(II) ions plus smaller amounts of allyl isothiocyanate and rhodanide ions to produce hair-growth stimulating actions. Pickart (e.g., WO 91/07431, 88/08695 and EP 288,278) found a number of metal complexes of derivatives of Gly-L-His-L-Lys to increase hair follicle size and the rate of hair-growth.

Despite the therapeutic promise of the above-mentioned metal complexes, toxicity and tissue irritation occur with many metal complexes (see, e.g., Johnson et al., *Inorg. Chem. Acta*, 67: 159–165 (1982); Pickart et al., *Biochem. Pharm.*, 32: 3868–3871 (1983); and Pickart et al., *Lymphokines* 8: 425–446 (1983)). For example, while copper-salicylate complexes and numerous copper-salicylate analogs possess anti-inflammatory activities, other salicylate analogs such as the copper(II) complex of salicylaldehyde benzoyl hydrazone are highly toxic to tissues. Similarly, copper(II)-Gly-L-His-L-Lys supports cellular viability and possesses anti-inflammatory and healing actions, yet close synthetic aroylhydrazone analogs of its copper-binding region are extremely toxic to cells and tissues.

Another problem with copper complexes for therapeutic use concerns the binding affinity of copper ion to the complexing molecule. While a defined copper-complex can be synthesized, its therapeutic use places the complex in the physiological milieu of the tissues where a plethora of literally hundreds of compounds compete for binding to the copper ion, which can form electrostatic bonds to as many as six separate molecules. If the copper is removed from the complex and becomes loosely bound, then tissue irritation occurs (see Raju et al., *J. Natl. Cancer Inst.*, 69: 1183–1188 (1982)).

Further complications arise when such metal complexes are formulated into carrier creams or ointments. Various chemicals are added to the formulations to increase adherence to skin and wound surfaces and to enhance the penetration of the complexes into the target tissue. Yet, since many of these substances also bind to the metals, the expected therapeutic benefits may be nullified or significantly attenuated. Also, detergents such as sodium dodecyl sulfate are used to help blend oil and water phases of the emulsions and stabilize the formulations. However, such detergents are themselves tissue irritants that can delay healing.

Another problem encountered with many of the metal complexes intended for therapeutic use is that they cannot be heat-sterilized; hence, to meet safety requirements, high concentrations of antimicrobial chemicals must be added during manufacture to inhibit the growth of microorganisms and the transmission of viruses. These antimicrobial agents may also inhibit the viability and function of a host's cells such as macrophages and fibroblasts that are involved in the maintenance and repair of skin and other tissue, and thus these agents may retard the healing response.

What is needed in the art are compositions useful in tissue protection, tissue healing, and/or stimulating hair growth, which compositions could be conveniently produced and at low cost. Preferably, the compositions could be sterilized without loss of bioactivity and could be formulated for topical application without the use of detergents or other potentially irritating compounds. The ideal composition would also adhere well to skin and other materials such as wound dressings (for example, adhesive bandages). To speed the time and expense required for regulatory approvals, the compositions would be prepared from materials that are generally recognized as safe by regulatory agencies and thus could be used with minimal safety concerns and regulatory barriers. Quite surprisingly, the current invention fulfills these and other related needs.

SUMMARY OF THE INVENTION

The present invention provides compositions and methods for accelerating the healing of topical wounds and skin irritation, for protecting skin from damaging effects of oxidation, and for increasing the size of hair follicles and the rate of hair growth in warm-blooded animals. The compositions useful in these methods, including pharmaceutical compositions, are prepared from starch pastes that are complexed with an ionic transition metal.

Thus, in one aspect the invention provides methods for preparing the pharmaceutical compositions useful in accelerating the healing of topical wounds or increasing hair follicle size and hair growth in a warm-blooded animal. A starch is combined with a useful amount of an aqueous solution of transition metal salt, then adjusted to a useful acidity range for skin products. Typically, the starch is conveniently obtained from plant products such as wheat, corn, or potatoes. The starch is then complexed to an ionic transition metal, such as copper(II) or and tin(II).

The resulting aqueous mixture is composed of complexes of the starch and the metal ions. The mixture can be adjusted, such as with water or the like, to produce a sticky paste-like mixture. The mixture may be used directly or combined with a pharmaceutically acceptable carrier to form a cream or lotion, in a concentration of from about 10% to about 50% starch-metal complex or more. The preparation may be sterilized or pasteurized, as desired, without destroying the healing or hair-growth stimulating activity of the starch-metal complex.

In other embodiments the invention provides methods for enhancing the recovery of skin of a warm-blooded animal from wounds, such as surgical incisions, burns, inflammation or minor irritation due to oxidative damage, etc. The methods comprise administering to the skin wound or irritation a therapeutically or, in some cases a prophylactically effective amount of a composition which comprises the starch-ionic transition metal complex. Due to the paste-like adhesiveness of the compositions of the invention re-application to the skin is minimized compared to other topical healants and formulations.

Yet other embodiments relate to compositions and methods for increasing hair follicle size and the rate of hair growth in warm-blooded animals, such as humans. The methods comprise administering to the skin in the area in which hair growth is desired an amount of starch-metal complex sufficient to increase hair follicle size and the rate of hair growth in said animal. Typically, the composition will be administered topically as a cream, and will be applied on a daily basis until hair growth is observed and for a time thereafter sufficient to maintain the desired amount of hair growth.

DESCRIPTION OF THE SPECIFIC EMBODIMENTS

Compositions and methods are provided by the present invention for treatments to protect damaged skin and thereby allow natural healing processes to proceed, to enhance tissue regenerative processes in the skin of warm blooded animals, and to stimulate hair growth in warm blooded animals. The composition are formed by the complexation of starches from various sources (e.g., wheat, corn, potatoes) and ionic transition metals, such as copper or tin.

The starch-metal complexes of the present invention are prepared from starches extracted from any of a variety of sources. Most conveniently the starches are those which are widely available at relatively low cost, such as wheat, corn, potato, oat, pea, bean, rice, soybean, and barley starch. Such starches are widely available from commercial sources. By "starch" is generally meant a high molecular weight carbohydrate polymer, often of the amylose or amylopectin form, with a molecular weight of the polymer typically being in excess of 100,000 Daltons.

To produce the starch-metal complexes useful in the present invention, the starch is complexed with one or more ionic transition metals, such as copper, indium, tin, zinc, or the salts thereof, such as sulfate, acetate, phosphate, etc. By complexed is meant that the starches and metal ions form electrostatic bonds, although this mechanism is offered by way of possible explanation only and not by way of limitation. In one method for preparing the starch-metal complex, the starch is mixed with sufficient water (at about room temperature, 22°–25° C.) to form a thick paste. To obtain this paste, wheat starch (1 gram) is mixed with about 10 ml of water, while corn starch (1 gram) and potato starch (1 gram) require only about 3 ml of water. The paste is then mixed with a aqueous solution of a metal salt (copper(II) chloride or tin(II) chloride, tin(IV) chloride, indium(III) chloride, or zinc(II) chloride) at a salt concentration of about 10 to 50% (w/v), more preferably about 20% (w/v). The volume of metal salt solution added is that amount needed to obtain a final metal concentration in the paste of 0.3 to 1.2% (weight/weight), although this concentration can vary considerably. The addition of the metal salt may reduce the pH of the paste to about 3.0, and thus the pH of the paste may be raised to 6.5, for example, by careful addition of 1N sodium hydroxide or the like. This pH is useful for skin preparations but other pH levels near neutrality or in the slightly acidic range are also efficacious.

The sticky paste can be applied directly to the skin or is formulated into skin creams and lotions at concentrations of usually 5 to 20% (w/w) although higher concentration are also effective. The thick paste can also be diluted with water to form a workable paste that spreads easily over the skin but does not run off.

The starch-metal complexes of the invention may be administered for a variety of therapeutic, prophylactic or cosmetic uses to humans or in veterinary applications to other warm-blooded animals. Among veterinary animals particularly well suited for treatment with the present compositions are species of equine, bovine, porcine, ovine, caprine, canine, avian, feline, etc.

The compositions and pharmaceutical preparations thereof are intended for local, topical, oral or parenteral (e.g., subcutaneous injection) administration for prophylactic and/or therapeutic or cosmetic treatment. Preferably, the pharmaceutical compositions are administered locally, e.g., topically, as a paste, cream or salve.

For administration to warm-blooded animals, the starch-metal compositions will typically be sterilized and incorporated into pharmaceutical or veterinary formulations. Compositions which comprise the starch-metal complexes can be sterilized by conventional, well known sterilization techniques, or by boiling or pasteurization, without substantially adversely affecting the biological activity of the starch-metal complexes. The compositions may contain pharmaceutically acceptable auxiliary substances as required to approximate physiological conditions and as necessary to prepare compositions for convenient administration, such an pH adjusting and buffering agents, and delivery vehicles. Actual methods for preparing pharmaceutically administrable compounds will be known or apparent to those skilled in the art and are described in detail in, for example, *Remington's Pharmaceutical Science,* Mack Publishing Co., Easton, Pa. (1985), which is incorporated herein by reference.

Depending on the intended mode of administration and the intended use, the compositions may converted to solid, semi-solid, or liquid dosage forms, such, for example, as powders, granules, crystals, liquids, suspensions, liposomes, pastes, cremes, salves, etc., and may be in unit-dosage forms suitable for administration of relatively precise dosages. The compositions may include a conventional pharmaceutical carrier or excipient and, in addition, may include other medicinal agents, growth factors, wound sealants, carriers, etc., as further described below.

For semi-solid compositions, as would be appropriate for pastes and creams intended for topical administration, the starch-metal complexes can be provided separately or may be compounded with conventional nontoxic carriers such as, for example, aloe vera gel, squalane, glycerol sterate, polyethylene glycol, cetyl alcohol, stearic acid, and propylene glycol, among others. Such compositions may contain about 5–100% active ingredient, more preferably about 20–40%. The concentration of the starch-metal complexes in these formulations can vary widely, and will be selected primarily by intended use, viscosities, etc., in accordance with the particular mode of administration selected. Actual methods of preparing such dosage forms are known, or will be apparent, to those skilled in this art; for example, see *Remington's Pharmaceutical Science,* supra. The composition or formulation to be administered will, in any event, contain a quantity of the starch-metal complexes sufficient to achieve the desired therapeutic or prophylactic effect in the subject being treated.

The tissue healing compositions of the invention are administered to a warm-blooded animal, such as humans, already suffering from a wound, oxidative skin damage, inflammatory skin lesions, as described above, in an amount sufficient to allow the healing process to proceed more quickly than if the host were not treated. In the case of an animal suffering from decreased hair follicle size and impaired hair growth, the compositions of the invention are administered in an amount sufficient to increase hair follicle size and the rate of hair growth. Amounts adequate to accomplish these effects are defined as a "therapeutically effective doses." Amounts effective for this use will depend on the severity of the wound, sore, etc., in the case of wound healing, and the extent of decreased follicle size in the case of impaired hair growth has, and the general state of health of the patient being treated, but generally range from about 1 mg to about 25 mg per day of starch-metal complex per day per square centimeter of wound site, with dosages of from about 5 mg to about 10 mg per day per square centimeter of wound site being more commonly used. Maintenance dosages over a prolonged period of time may be adjusted as necessary. For veterinary uses higher levels may be administered as necessary. Determining actual amounts of the starch-metal complexes necessary to treat a particular wound or condition as described above will be through standard empirical methods well known in the art.

In prophylactic applications compositions containing the starch-metal complexes are administered to a host susceptible to or otherwise at risk of skin lesions or similar damage, to enhance the host's own wound healing or anti-oxidative capabilities. Such an amount is defined to be a "prophylactically effective dose." In this use, the precise amounts again depend on the host's condition and general state of health, but generally range from about 0.1 mg to about 10 mg per day per square centimeter of skin, more commonly from about 1 mg to about 3 mg per $cm^2$ of skin per day. Single or multiple administrations of the compositions can be carried out.

The starch-metal complexes of the invention may be administered in relatively large amounts without serious side effects, although indiscriminate use may produce discoloration of the skin. In instances where the compositions are administered to inhibit oxidative or biochemical damage to the skin or to those suffering from only mild or irritation or inflammation of the skin, the dose may be adjusted accordingly to lower maintenance levels.

The compositions of the invention, including pharmaceutical compositions, may be administered alone or as adjunct therapy or prophylaxis. The starch-ionic transition metal compositions can be used in combination with other compositions, such as described in commonly owned pending patent applications U.S. Ser. No. 07/954,620 filed Sep. 29, 1992, now U.S. Pat. No. 5,382,431, and U.S. Ser. No. 08/219,047 and U.S. Ser. No. 08/218,392, filed Mar. 28, 1994, each of which is incorporated herein by reference in its entirety, or with other growth factors known to improve other aspects of healing. In this manner, a synergistic effect may be attained that yields a clinical efficacy greater than that realized with any single factor. Further, while the compositions described herein stimulate a spectrum of healing processes, clinical wounds may differ considerably in their properties and healing patterns, leading one to utilize a combination of a composition described herein and another factor. For example, nerve regeneration is defective in many burns and thus one can add a specific nerve growth factor to the composition to enhance nerve regrowth into the burn area. Examples of factors with other reported healing properties include epidermal growth factor, fibroblast growth factor, nerve growth factor, transforming growth factors, angiogenic growth factors, heparin, fibronectin, fibrin, platelet-derived growth factor, enzymatic superoxide dismutase, extracts of blood or factors from the blood, and other similar factors.

The following examples are offered by way of illustration, not by way of limitation.

EXAMPLE I

Preparation of Active Starch-Metal Complexes

This Example describes methods used in the preparation of the starch-metal complexes having biological activities described further below.

Wheat starch, corn starch, and potato starch were purchased from Sigma Chemical Company, St. Louis, Mo., as was cupric chloride hydrate (no. C 6641). Tin (II) chloride, 99% pure was purchased from Aldrich Chemical Company, Milwaukee, Wis.

In one method for preparing the starch-metal complex, a starch was mixed with sufficient water (at about 23° C.) to form a thick paste. To obtain this paste, wheat starch (1 gram) was mixed with 10 ml of water, while corn starch (1 gram) and potato starch (1 gram) required only about 3 ml of water. The paste was then mixed with a aqueous solution of copper(II) chloride or tin(II) chloride, at a salt concentration of 20% (w/v), where the volume of metal salt solution added was that amount needed to obtain a final metal concentration in the paste of about 0.3 to 1.2% (weight/weight). The addition of the metal salt reduced the pH of the paste to about 3.0. The pH of the paste was then raised to 6.5 by careful addition of 1N sodium hydroxide. This pH is useful for skin preparations but other pH levels near neutrality or in the slightly acidic range are also efficacious.

The starch-copper complexes are used as skin protective agents that serve as a skin barrier over damaged or irritated skin. The glue-like paste adheres to the skin and forms a protective barrier. Damaged or irritated skin healed strikingly faster after treatment with such a composition.

As described further below, the starch-copper and starch-tin complexes were used to promote hair growth and the enlargement of hair follicles. In hair growth models in mice, application of these complexes to the skin produced a marked stimulation of hair growth after 8 to 12 days.

Other types of starch-metal complexes from other plants and other metal salts of the metals, such as sulfate, acetate, phosphate and so forth would be expected to work similarly.

EXAMPLE II

Healing of Surgical Wounds with Starch-Copper Complexes

This Example describes the use of a paste prepared with the starch-copper complexes to hasten the healing of surgical incision wounds in animals.

Surgical incisions (1.25 cm) were made on the backs of anesthetized, 35 gram, Swiss-Webster mice. Immediately after surgery and 24 hours later, the wounds were covered with a thin film of the paste containing the active starch-copper complexes in Example I above. Control wounds were untreated or received starch without the metal complexed thereto. As seen in Table 1, wounds treated with the active starch-copper complex healed faster than control wounds. Since rapidly healing wounds tends to contract and become more rounded, the healing activity can be related to the length of the wound after 9 days. Each group consisted of eight mice.

TABLE 1

Effect of starch-copper complex on incision length.

| Test group | Length of wound after 9 days (cm.) |
| --- | --- |
| Control | 0.91 ± 0.12 |
| Wheat starch-no copper | 0.88 ± 0.19 |
| Wheat starch-1.0% copper complex | 0.25 ± 0.09 |
| Wheat starch-0.3% copper complex | 0.37 ± 0.09 |
| Cornstarch-no copper | 0.98 ± 0.23 |
| Corn starch-1.0% copper complex | 0.31 ± 0.14 |
| Corn starch-0.3% copper complex | 0.40 ± 0.06 |
| Potato starch-no copper | 0.92 ± 0.19 |
| Potato starch-1.0% copper complex | 0.41 ± 0.15 |
| Potato starch-0.3% copper complex | 0.47 ± 0.14 |

EXAMPLE III

Healing of Burn Wounds with Starch-Copper Complex

This Example demonstrates the increased healing of burn wounds in animals using the starch-copper compositions applied topically.

Second-degree burns were induced on the shaved backs on anesthetized mice by placing a circular (1.25 cm diameter, wound area=1.22 cm$^2$) brass rod (temperature 100° C.) in contact the skin for 7 seconds. Immediately after burning, and 24 and 48 hours later, the wounds were covered with a thin film of the paste containing the active starch-copper complex of Example I above. Control wounds were untreated. Wounds were traced on anesthetized mice, digitized from an computerized scanning bed, and area calculated from the computerized pixel number. Burns treated with the active starch copper complexes showed less post-burn inflammation and healed markedly faster than untreated control wounds. Each group consisted of 8 mice.

TABLE 2

Effect of starch-copper complex on burn wounds.

| Test group | Area of wound after 15 days (cm2) |
| --- | --- |
| Control | 0.90 ± 0.17 |
| Wheat starch-0.3% copper complex | 0.34 ± 0.13 |
| corn starch-0.3% copper complex | 0.33 ± 0.09 |
| Potato starch-0.3% copper complex | 0.42 ± 0.12 |

EXAMPLE IV

Reduction in Post-Burn Inflammation of Skin

This Example demonstrates the ability of starch-copper complex to reduce inflammation associated with mild skin burns.

Very mild thermal burns were induced on the shaved backs of anesthetized mice (8 mice in each group) by a placing a circular (1.25 cm diameter, irritated area=1.22 cm$^2$) brass rod (60° C.) in contact the skin for 5 seconds. This produced a mild skin irritation characterized by redness and swelling, but rarely a loss of skin tissue. Immediately after inducing the thermal injury, the irritated area was covered with a thin film of the paste containing one of the following active complexes from Example I: wheat starch with 0.3% copper ion, corn starch with 0.3% copper ion, or potato starch with 0.3% copper ion. Control wounds were untreated or received starch that did not contain the metal complex. Wounds were observed at daily intervals. At day 3, the thermal injuries of the controls were still reddish and swollen while the skin with any of the three starch-copper complexes had minimal reddishness and swelling.

EXAMPLE V

Pasteurization of Active Starch-Copper Composition

Pasteurization consists of heating a solution to 160° F. for 30 minutes which kills all but the hardiest microorganisms. For this test, various starches were complexed with copper chloride by the methods described above in Example I. The resultant paste was thoroughly mixed, the pH raised to pH 6.5, then heated to 160° F. for 30 minutes. After cooling to room temperature, the pastes were applied to surgical incision wounds in mice in the manner described in Example II. Healing activity was similar to that observed with unpasteurized active composition, as shown in Table 3. Each group had six mice.

TABLE 3

Effect of pasteurization on active complex.

| Test group | Length of wound after 9 days (cm) |
| --- | --- |
| Control | 0.89 ± 0.15 |
| Wheat starch-1.0% copper complex | 0.29 ± 0.13 |
| Corn starch-1.0% copper complex | 0.35 ± 0.16 |
| Potato starch-1.0% copper complex | 0.47 ± 0.21 |

EXAMPLE VI

Sterilization of Active Composition by Boiling

This Example demonstrates that the starch-copper complex can be sterilized by boiling and yet retains substantially all of the activity of the unsterilized formulation. This presents considerable advantage by avoiding the necessity of include sensitizing antimicrobial agents in the compositions.

Sterilization by boiling kills virtually all microorganisms. For this test, 10 grams of soybean starch were complexed with copper chloride by the procedure described above in Example I. After adding the copper chloride solution to the solution of soybean starch, the resultant solution was thoroughly mixed, the pH raised to pH 6.5, then heated in a boiling water bath for 10 minutes. After cooling to room temperature, the active composition was prepared as described above in Example I, then applied to surgical wounds in mice in the manner described in Example II. The healing activity observed with the sterilized starch-copper complexes were similar to results obtained with unsterilized active compositions. Each group had six mice.

TABLE 4

Effect of sterilization on active starch-metal complexes.

| Test group | Length of wound after 9 days (cm) |
|---|---|
| Control | 0.89 ± 0.15 |
| Wheat starch-1.0% copper complex | 0.31 ± 0.16 |
| Corn starch-1.0% copper complex | 0.39 ± 0.19 |
| Potato starch-1.0% copper complex | 0.42 ± 0.18 |

EXAMPLE VII

Adherence of Starch-Copper Paste to Skin

This Example describes the use of a starch-copper active complex to improve the adherence of a wound dressings to the surface of the skin. The starch-copper complexes can thus be used to more effectively cover and seal wounds with dressings. Also, many tapes used to hold medical sensors to the skin or catheters in veins cause skin irritation. The incorporation of a starch-copper complex into the adhesive used on such tapes will reduce such skin irritation and injury. For testing, the wound coverage portion of an adhesive bandage (Band Aid™ brand) was cut away from the adhesive portion. The wound coverage portion of the tape, which has no skin adhesive qualities, was covered with the wheat starch complexed with 0.3% copper ion. The paste-covered tape was applied to the upper arm of humans and left in place during normal work functions in an office. The tape adhered well to the skin during the subsequent 8 hour test. This demonstrated that such wound-healing pastes possessed significant adhesive properties on human skin.

EXAMPLE VIII

Stimulation of Hair Growth

This Example describes the use of compositions containing starch-metal complexes to stimulate the growth of hair follicles in warm blooded animals.

The model used in this test was a mouse model that has been found to successfully predicts the therapeutic response in humans (see, e.g., U.S. Pat. No. 5,118,665, which is incorporated herein by reference). Hair growth in mammals proceeds through actively growing stages (anagen) followed by dormant stages (telogen). The test method generally involves applying the hair-growth stimulant to the skin of mice in telogen phase. Female, Swiss-Webster mice begin a telogen phase at about 45 days of age that lasts until about 90 days of age. After application of the active substance, enhanced hair growth is noted within 10 to 14 days. For this test, mice 50 days of age were used.

Starch compositions containing copper(II) and tin(II) were tested. For testing, the starch-metal pastes were mixed with saline (25% starch composition and 75% physiological saline by weight). Mice were shaved, then 0.05 ml of the mixture was infiltrated immediately below the skin by injection. Control mice were injected with an equal volume of saline or with starch not containing the metal. Each group contained 10 mice. After 12 days, the groups were compared. The percentage of mice with hair growth at the injection site and the relative strength of the hair growth response (on a scale of 1 to 5 where 1 is barely noticeable growth and 5 is very strong hair growth) were determined.

The results, shown in Table 7, indicate that all composition were active hair growth stimulants, with starch-tin(II) complexes being the most effective agent.

TABLE 5

Stimulation of Hair Growth by Starch-Metal Complexes.

| | Percent with hair growth at injection site | Average intensity of hair growth |
|---|---|---|
| Control mice | 0 | 0 |
| Wheat Starch- no copper(II) | 0 | 0 |
| Wheat Starch-1% copper(II) | 90 | 2.5 |
| Wheat Starch-1% tin(II) | 100 | 4.0 |

EXAMPLE IX

Stimulation of Hair Growth by Topical Application

The model used in this Example was as described in Example X except that the active starch-metal pastes were applied topically to the skin. The animals were shaved, then 0.10 grams of the paste applied to the shaved area as smoothly as possible for four consecutive days. Control animals were swabbed with saline or starch not complexed with the metal. Each group contained 10 mice. After 14 days, the mouse groups were compared. The percentage of mice with hair growth in the center of the shaved area and the relative strength of the hair growth response (on a scale of 1 to 5 where 1 is barely noticeable growth and 5 is very strong hair growth) were determined. All composition were active, with tin(II) being the most effective agent.

Topical Application of Starch-Metal Complexes to Stimulate Hair Growth.

| | Percent with hair growth in center of shaved area | Average intensity of hair growth |
|---|---|---|
| Control mice | 10 | 0.2 |
| Wheat starch | 10 | 0.0 |
| Wheat starch-1% copper(II) | 90 | 2.0 |
| Wheat starch-1% tin(II) | 100 | 4.0 |

It is evident from the above results that the subject invention provides compositions of starch-metal complexes for topical skin, wound and surgical treatments to protect damaged skin and facilitate natural healing processes, to enhance tissue regenerative processes in the epidermis, and to stimulate hair growth in warm blooded animals. The invention also provides economical methods for preparing and formulating the compositions for topical administration.

Although the foregoing invention has been described in some detail by way of illustration and example for purposes of clarity of understanding, it will be obvious that certain changes and modifications may be practiced within the scope of the appended claims.

What is claimed is:

1. A method for accelerating the healing of topical wounds in a warm-blooded animal which comprises:
    administering to the wound a therapeutically effective amount of a composition which comprises a starch complexed with an ionic metal.
2. The method of claim 1, wherein the ionic metal is copper(II), and therapeutically acceptable salts thereof.
3. The method of claim 1, wherein the ionic metal is tin(II).

4. The method of claim 1, wherein the starch is obtained from wheat, corn, potato, or soybean.

5. A method for enhancing the recovery of skin of a warm-blooded animal from irritation, comprising administering to the skin irritation a therapeutically effective amount of a composition which comprises a starch complexed with an ionic metal.

6. The method of claim 5, wherein the ionic transition metal is copper(II).

7. The method of claim 5, wherein the starch complexed with the ionic metal is obtained from wheat, corn, potato, or soybean.

8. A method for protecting the skin from oxidative damage and aiding the recovery of skin wounds in a warm blooded animal, comprising:

administering to the skin or wound site a prophylactically or therapeutically effective amount of a composition which comprises a starch complexed with an ionic metal.

9. The method of claim 8, wherein the ionic metal is copper(II), and therapeutically acceptable salts thereof.

10. The method of claim 8, wherein the starch is prepared from wheat, corn or potato or soybean.

11. A pharmaceutical composition useful for accelerating the healing of topical wounds of a warm-blooded animal which comprises a therapeutically effective amount of a starch complexed with an ionic transition metal and a pharmaceutically acceptable carrier.

12. The pharmaceutical composition of claim 11, wherein the ionic metal is copper(II) or tin(II), and therapeutically acceptable salts thereof.

13. The pharmaceutical composition of claim 11, wherein the starch is from wheat, corn, soybean or potato.

14. The pharmaceutical composition of claim 11, wherein the starch-metal complex is present in the composition at a concentration of 10% to 50%.

15. A pharmaceutical composition for increasing hair follicle size and rate of hair growth in a warm-blooded animal, which comprises a hair growth stimulating amount of a starch-ionic metal complex and a pharmaceutically acceptable carrier.

16. The pharmaceutical composition of claim 15, wherein the starch-metal complex is present in the composition at a concentration of 5% to 25%.

17. The pharmaceutical composition of claim 15, wherein the ionic metal is copper(II) or tin(II), and therapeutically acceptable salts thereof.

18. The pharmaceutical composition of claim 15, wherein the starch is from wheat, corn, soybean or potato.

* * * * *